(12) United States Patent
Bergstrom et al.

(10) Patent No.: US 9,278,297 B2
(45) Date of Patent: Mar. 8, 2016

(54) METHOD FOR ION-EXCHANGE CHROMATOGRAPHY AND MEDIA USED THEREOF

(75) Inventors: Jan Bergstrom, Balinge (SE); Bo-Lennart Johansson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 496 days.

(21) Appl. No.: 13/809,179

(22) PCT Filed: Jun. 28, 2011

(86) PCT No.: PCT/SE2011/050852
§ 371 (c)(1),
(2), (4) Date: Jan. 9, 2013

(87) PCT Pub. No.: WO2012/005664
PCT Pub. Date: Jan. 12, 2012

(65) Prior Publication Data
US 2013/0115709 A1    May 9, 2013

(30) Foreign Application Priority Data
Jul. 9, 2010  (SE) ..................................... 1050774

(51) Int. Cl.
*G01N 30/02* (2006.01)
*B01D 15/36* (2006.01)
*C07K 1/18* (2006.01)

(52) U.S. Cl.
CPC ................ *B01D 15/361* (2013.01); *C07K 1/18* (2013.01)

(58) Field of Classification Search
CPC ........... A61K 2039/6031; A61K 47/42; A61K 39/39; A61K 47/48238; A61K 47/48315; A61K 38/02; A61K 38/10; A61K 9/5052; A61K 47/48853; A61K 47/48884; A61K 49/0056; C12Q 2527/125; G01N 33/6803
See application file for complete search history.

(56) References Cited

FOREIGN PATENT DOCUMENTS

| CN | 101336133 | 11/2006 |
|---|---|---|
| WO | WO 2004/011592 | 2/2004 |
| WO | WO 2005/079984 | 9/2005 |
| WO | WO 2007/054548 | 5/2007 |
| WO | WO 2010/005364 | 1/2010 |

OTHER PUBLICATIONS

Search Report Dated May 6, 2014 Issued on Corresponding Chinese Patent Application No. 201180033702.4.
Ahamed, T., et al., Journal of Chromatography A, 1164 (2007) 181-188.
Hirsh, A., et al., American Biotechnology Laboratory, Oct. 2008.

*Primary Examiner* — Yelena G Gakh
(74) *Attorney, Agent, or Firm* — Parks Wood LLC

(57) ABSTRACT

The present invention relates to a method for running ion exchange chromatography on a media comprising shell beads having an inner porous core and an outer shell, wherein the inner core is provided with ligands whose charge changes with pH and the shell is provided with charged ion exchange ligands, the method comprising the following steps: a) adsorbing sample molecules on the shell ligands at a first pH; b) causing a discharge of the inner core ligands at a second pH by addition of a buffer substance that is able to increase its charge having the same sign/type as that of the core ligands, which at the same time causes release of ions from the inner core ligands and thereby an increase in ionic strength that displaces the sample molecules from the shell ligands i.e. causes an elution.

10 Claims, 2 Drawing Sheets

METHOD FOR ION-EXCHANGE CHROMATOGRAPHY AND MEDIA USED THEREOF

CROSS-REFERENCE TO RELATED APPLICATIONS

This application is a filing under 35 U.S.C. 371 of International Application No. PCT/SE2011/050852, filed Jun. 28, 2011, published on Jan. 12, 2012 as WO 2012/005664, which claim priority to application number 1050774-7 filed in Sweden on Jul. 9, 2010.

FIELD OF THE INVENTION

The present invention relates to novel ion exchange media and use thereof. More closely, the invention relates to a method for running ion exchange chromatography on a media comprising shell beads. The media comprises ligands in the core whose charge change with pH and ion exchange ligands able to bind the sample molecules in the outer shell.

BACKGROUND

Within biotechnology, the chromatographic methods suggested up to date are based on different modes of interaction with a target. Thus, for example, in ion-exchange chromatography, the functional groups are permanently bonded ionic groups with their exchangeable counter ions of opposite charge.

Chromatographic media normally used for ion exchange chromatography of biomolecules are substituted with a suitable charged ligands homogeneous distributed in the beads. To accomplish the salt-gradient and/or the pH-gradient for elution of adsorbed biomolecules a gradient is obtained by using to two pumps with different eluents. Initially the non-displacing mobile phase pump conveys most (if not all) and the displacing mobile phase pump very little (or even nothing) of the flow through a chromatography media. The flow-rate of each pump is then modified either continuously or intermittently to obtain gradients suitable for elution of adsorbed compounds.

A simpler method of running ion exchange chromatography than using the conventional two pump setups for generation of salt-gradient and/or the pH-gradient for elution of adsorbed sample molecules would be desirable in many instances.

SUMMARY OF THE INVENTION

The present invention provides a new principle of running ion exchange chromatography which is not dependent on two pump setups for generation of salt-gradient and/or the pH-gradient for elution of adsorbed sample molecules.

In a first aspect, the invention provides a method for running ion exchange chromatography on a media comprising shell beads having an inner porous core and an outer shell, wherein the inner core is provided with ligands whose charge changes with pH and the shell is provided with charged ion exchange ligands, the method comprising the following steps: a) adsorbing sample molecules on the shell ligands at a first pH; b) causing a discharge of the inner core ligands at a second pH by addition of a buffer substance that is able to increase its charge having the same sign/type as that of the core ligands, which at the same time causes release of ions from the inner core ligands and thereby an increase in ionic strength that displaces the sample molecules from the shell ligands i.e. causes an elution.

Any type of buffer substance, for example an amine buffer, may be used as long as it is of the same type (having the same type of charge) as the core ligands, for example amine-ligands. This will give increased ionic strength when pH increases according to the following:

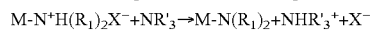

M=bead matrix

Preferably, the outer shell ligands are strong ion exchange ligands, for example $-N^+(CH_3)_3$ and all types of quatenary ammonium ligands, non aromatic and aromatic $-SO_3^-$ ligands.

In a preferred embodiment, the charge change per pH unit of functionalized core is >30 μmol/pHmL gel.

According to the method of the invention the shell ligands and core ligands may have the same or different charge and are selected from any type of cation ligands, such as carboxylate ($-COO^-$), phosphonate or phosphate ($-PO_3^{2-}$, $-P(OH)O_2^-$, and $-OP(OH)O_2^-$, $-OPO_3^{2-}$ respectively), sulphonate or sulphate ($-SO_3^{31}$ and $-OSO_3^-$ respectively), -aryl-O$^-$ (phenolate/arylolate) or any type of anion ligands, such as different nitrogens that are positively charged; for instance primary ammonium, secondary ammonium, tertiary ammonium, quaternary ammonium and amidinium.

Method according to one or more of the above claims, wherein the porosity of the core prevents or allows sample molecule to penetrate into the core.

Preferably the shell beads have a diameter between 3 to 400 μm and the outer shell is 0.5-100 μm thick. For example, in case of shell beads with a diameter of 100 μm the outer shell is 0.5-10 μm. In case of shell beads with a diameter of 300 μm the outer shell is 0.5-30 μm.

In an alternative embodiment, when the method is run in column format, the direction of flow is reversed in the elution step, i.e. the column is turned upside down. This enables sufficient time for ionic strength build-up and accomplishes shorter transportation distance of the sample molecules through the chromatographic bed resulting in sharp peaks.

In a second aspect the invention relates to chromatography media for use in the above method, comprising shell beads having an inner porous core and an outer shell, wherein the inner core is provided with ligands whose charge changes with pH and the shell is provided with charged ion exchange ligands.

In a third aspect, the invention relates to use of the above chromatography media for ion exchange chromatography of sample molecules of biological and synthetic origin, such as cells and/or parts thereof, virus and/or parts thereof, proteins, complexed proteins, fusion proteins, peptides, nucleic acids, amphoteric macromolecules, amphoteric particles, drugs, drug fragments.

The use may be in column, microtiter or batch format.

DETAILED DESCRIPTION OF THE INVENTION

Figure 1:
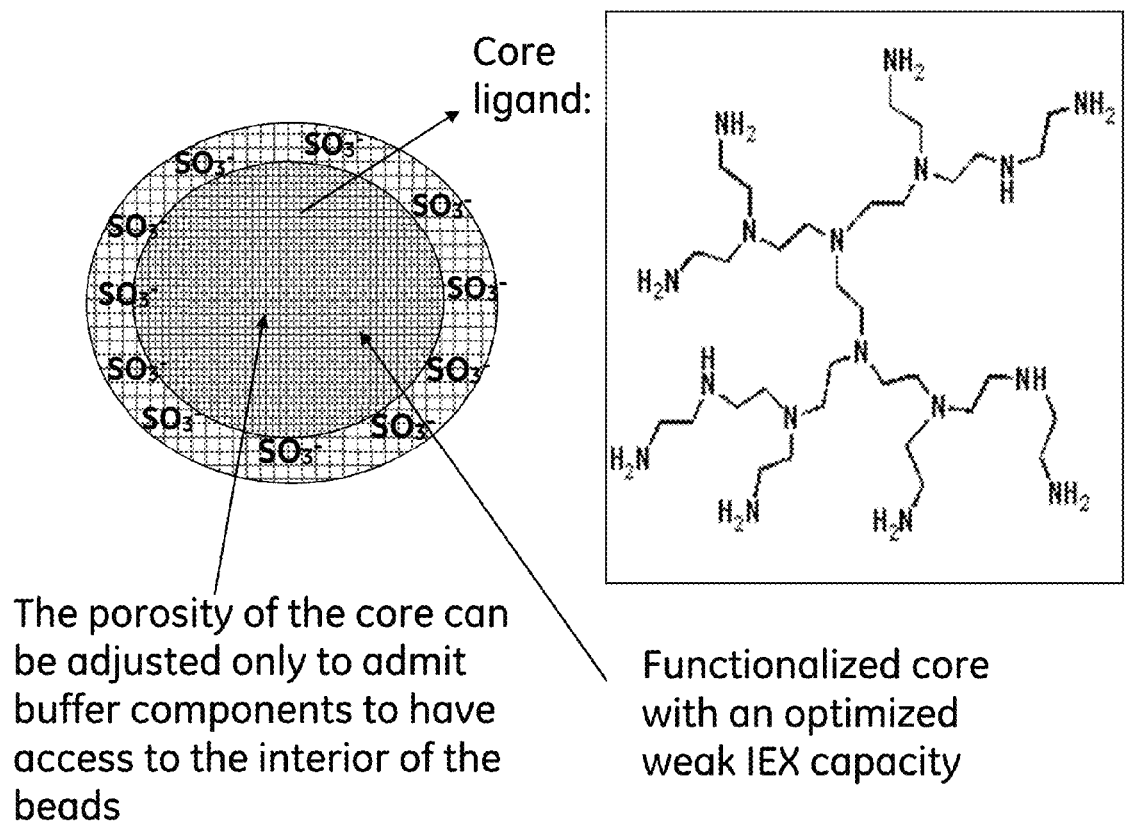
FIG. 1 shows bead design for a cation exchange medium with core ligands whose charge and ability to bind associated counter ions can be changed by a shift in pH.

This invention suggests using "shell beads" with a core functionalized with protonatable and de-protonatable functional groups (weak ion exchange ligands) which can reduce its charge or be discharged by changing the pH with a (buffer) compound that in turn in the process increases its charge and at the same time change the ionic strength in the surrounding solution (the mobile phase) and accomplish the elution of proteins adsorbed to charged preferable strong ion exchange ligands.

The ion exchange ligands aimed for sample adsorption are preferable attached in an outer thin shell and the core ligands are weak ion exchange ligands with a pKa allowing a charge change for the application in a suitable pH range and the core ligands can be both of the same charge or oppositely charged compared to the shell ligands. The core ligands can be, depending on the their chemical structure, chosen in order to give a change of charge by a relatively sharp pH switch in a short pH interval or a slow gradual change of charge in a broad pH interval. The latter types of ligands may be used to generate a pH and salt gradient in a chromatography column. Compared to chromatofocusing media according to co-pending SE patent application 1050157-5, the ligand density in the core of the invention will be several times higher in order to release a high enough amount of salt ions. The porosity of the core can be adjusted to exclude proteins/peptides in order to avoid binding of sample substituents. Furthermore, the mobile phase can use simple mixtures of "normal" buffering species able to discharge the core ligands and at the same time acquire charge with the same sign and thus allow the release of counter ions from the core ligands. Of course only one pump (no eluent mixing apparatus) will be necessary to obtain the increased ionic strength in and around the beads. The main application area of this type of media is large scale polishing of proteins and peptides. This type of bead is also very suitable for analytical applications.

The invention will now be described in association with the drawings and and experimental part.

EXPERIMENTAL PART

The present examples are presented herein for illustrative purpose only, and should not be construed to limit the invention as defined by the appended claims.

General

Volumes of matrix refer to settled bed volume and weights of matrix given in grams refer to suction dry weight (swelled beads with void water removed). For reaction stirring, a motor-driven stirrer was used. Conventional methods were used for the analysis of the functionality and the determination of the degree of allylation, or the degree of amine content on the beads. One way to prepare a separation matrix according to the invention is exemplified below, starting from a crosslinked agarose gel (Sepharose™ HFA 55, GE Healthcare, Uppsala, Sweden). The bead diameter of Sepharose HFA 55 is about 90 µm.

Preparation of Shell Media for Isocratic Ion Exchange Chromatography with Internal pH and Ionic Strength Gradient Elution Based on Sepharose HFA 55-HFA 55 Core-PEI Shell-$SO_3^-$ Allyl Activation of Sepharose HFA 55

Sepharose HFA 55 was washed with distilled water on a glass filter. The gel, 800 mL drained gel, was added into a 3-necked round bottomed flask. NaOH (800 mL, 50%-solution) was added and mechanical stirring was started and the slurry heated to 50° C. on a water bath. After approximately one hour, 168 mL of allyl glycidyl ether (AGE) was added. The slurry was then left under vigorously stirring over night. After about 20 hours the slurry was transferred to a glass filter and washed with distilled water (×5), ethanol (×2) and distilled water (×5). The allyl content was then determined by titration; 230 µmol/mL.

Shell Activation (Partial Bromination)

Allylated gel, 100 mL, was weighed into a flask and 1000 mL of distilled water was added. 0.354 mL bromine was dissolved in 100 mL distilled water this solution was added to the allylated gel slurry. This amount of bromine corresponds to a shell thickness of about 5 µm. The bromine solution was added to the allyl gel slurry in 5 equivalent portions during vigorous stirring. After approximately 10 minutes the gel was washed with distilled water on a glass filter.

Shell Coupling of the Cation Exchange Groups (S-shell Prototype)

100 mL of the partially brominated gel (see above) was transferred to a flask and mixed with 12.5 g of sodium sulphite dissolved in 25 mL distilled water. While stirring, 50% NaOH is added to pH 12, followed by stirring for 20 h at 50° C. The gel was then washed on a glass filter with distilled water.

The ion exchange capacity was estimated to 25 µmol/mL.

Coupling of PEI (polyethyleneimine) in the Core of Beads 25 mL of S-shell gel (see above) was mixed with distilled water (25 mL) and 0.5 g sodium acetate in a beaker with overhead stirring. Bromine was added until the slurries had a remaining deeply orange/yellow colour. After 2 minutes of stirring, sodium formate was added until the slurries were completely discoloured. The gels were then washed with distilled water on a glass filter.

25 mL of drained core brominated gel were transferred to a beaker and mixed with 10 mL of water and 10 g polyethylenimine (750 000 g/mol). The mixtures were then stirred at 20° C. for 20 h, followed by washing with distilled water on a glass filter. The ion exchange capacity of the PEI functionalized core of the gel was estimated to 150 µmol/mL gel bed.

Chromatographic Evaluation of HFA 55 Core PEI Shell-S

To test the behaviour of the shell media prototype (HFA 55 Core PEI Shell-S) a column was packed with a mix of the S-shell prototype (see above) and HFA 55 Core PEI Shell-S. The use of 50% of the prototype HFA 55 Core PEI Shell-S was only a way to prove the efficiency of the medium (HFA 55 Core PEI Shell-S) to produce a pH-gradient and an ionic strength step/gradient.

Experimental

The mixture of the shell media (see above), with respect to chromatographic performance, were packed in HR 5/20 columns and the sample was injected (100 µL Ribonuclease A, 10 mg/mL) into the column after equilibration with buffer solution (50 mM formic acid, pH 2.7). The flow-rate was adjusted to 0.25 mL/min and the protein (Ribonuclease A) was eluted "isocratically" by applying the buffer B (300 mM Triethanolamine, pH 9.7).

Sample

The sample was Ribonuclease A dissolved in 50 mM formic acid, (pH 2.7) and the concentration was adjusted to 10.0 mg/ml. The sample volume was 100 µL.

Instrumental

LC System: Äkta Explore 10

Software: Unicorn

Column HR 5/20

Results and Discussion

To make improvements to downstream chromatographic platform resulting in major simplification of protein manufacturing it is highly important to keep or increase the chromatographic performance of separation media. In the present invention we suggest ion exchange beads which can in a column under an isocratic run generate an internal pH change or pH gradient and a superimposed ionic strength step/gradient. The separating ligands are attached in the shell and the ligands used in the elution process in the core. The charge of the core ligands can be switched by an eluent/buffer adjusted to a different pH compared to an earlier equilibration pH and thereby generate pH gradients and an ionic strength changes. In addition, the porosity of the core can be adjusted to exclude proteins/peptides. The design of this type of beads is illustrated in FIG. 1 for cation exchange chromatography.

In FIG. 1 we have suggested PEI (polyethylene imine) as the dischargeable IEX core ligand (other dischargeble IEX ligands can of course be used) which makes it possible to generate a gradual charge shift and pH-gradient between pH 3 to 10 at least. The core ligands for this type of beads are equilibrated and presaturated with the counter ions of the equilibration and adsorption buffer or a separate equilibration buffer with a higher concentration of buffer substances adjusted to a pH at which the core ligands are charged (i.e. in the case of anion exchange ligands with an acidic buffer, pH of e.g. 3) and then eluted with for example a triethanolamine buffer adjusted to 10. The charged buffer components in the mobile phase used in the elution step are due to their low concentration not by them self able to displace/elute bound (in this example positively charged) sample bio molecules from the $—SO_3^-$ groups. The titration with the high pH triethanol amine buffer of the nitrogens in the PEI ligands results in a decrease of their charge and a release of counter ions from the PEI ligands when pH increases. The released ions will in turn act as counter ions to the buffer compounds that in the titration process has acquire an increased charge. In this way an increased ionic strength in the mobile phase in and around the beads is generated. It will be possible to obtain an internal generated ionic strength gradient in addition to the pH-gradient by a slow titration of the PEI ligands with an amine buffer solution adjusted to a pH were the amine is not fully protonated or not protonated at all. This increase in ionic strength can be reinforced by using a high PEI density in the core of the beads.

Figure 2:
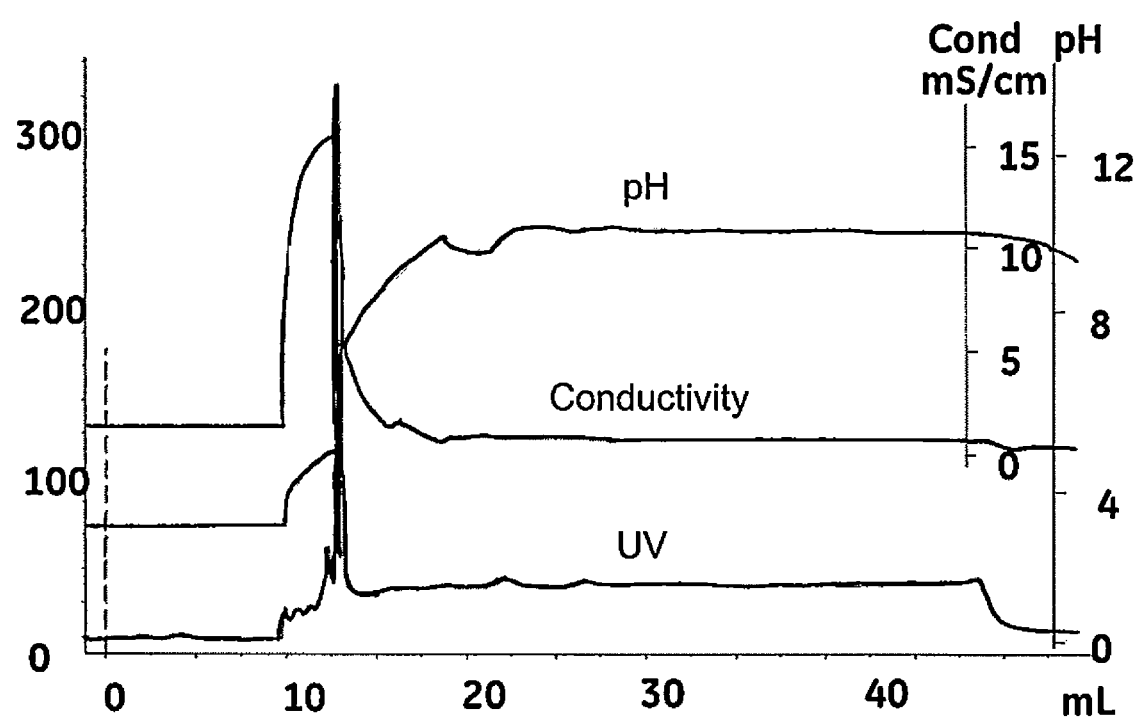
FIG. 2 shows separation of Ribonuclease A on a column packed with 50% of the prototype HFA 55 Core PEI Shell-S (weak anionic ligands) and 50% of the S-shell (strong cationic) prototype (see the experimental section for details).

To prove that this type of media can be used for separation of proteins a column was packed with 50% of the prototype HFA 55 Core PEI Shell-S and 50% of the S-shell prototype (see above). According to FIG. 2 a pH-gradient is obtained and a step in the conductivity is also observed. Ribonuclease A is nicely eluted in a sharp peak. The result clearly shows that this type of bead design (FIG. 1) can be used for purification of proteins. The performance of the beads can be optimized by adjusting the shell thickness, type of buffering ligands in the core and the ligands in the shell.

Advantageously, the direction of flow in the column is changed for elution. This enables sufficient time for ionic strength build-up and accomplishes shorter transportation distance of the sample molecules through the chromatographic bed resulting in sharp peaks.

The invention claimed is:
1. A method for running ion exchange chromatography, the method comprising the following steps:
   a) providing an ion exchange chromatographic media comprising shell beads having an outer shell and an inner porous core, wherein said outer shell has strong ion exchange ligands and said inner core is functionalized with weak ion exchange ligands;
   b) injecting a sample containing charged molecules onto said media thereby causing the sample molecules to be absorbed on the outer shell ligands at a first pH;
   c) modifying the pH of the sample by applying a buffer having a second pH, thereby causing a decrease in charge in said inner core ligands and a release of ions that displaces the sample molecules from the outer shell ligands and causes the sample molecules to be eluted from the media.

2. The method of claim 1, wherein the strong ion exchange ligands comprise $—N^{30}(CH_3)_3$ and all types of quaternary ammonium ligands and non aromatic and aromatic $—SO_3^-$ ligands.

3. The method of claim 1, wherein the charge change per pH unit of functionalized core is >30 µmol/pH·mL media.

4. The method of claim 1, wherein the outer shell strong ion exchange ligands and said inner core weak ion exchange ligands have the same or different charge and are selected from cation ligands and anion ligands.

5. The method of claim 1, wherein the porosity of said inner core prevents sample molecules from penetrating into said inner core.

6. The method of claim 1, wherein the porosity of said inner core allows sample molecules to penetrate into said inner core.

7. The method of claim 1, wherein the shell beads have a diameter between 3 to 400 µm.

8. The method of claim 7, wherein the outer shell is 0.5-100 µm thick.

9. The method of claim 1, wherein the method is run in column format and the direction of flow is reversed in the elution step.

10. A chromatography media comprising shell beads having an inner porous core and an outer shell, wherein said outer shell has strong ion exchange ligands and said inner core is functionalized with weak ion exchange ligands wherein the density of the weak ion exchange ligands is effective to cause charge change per pH unit >30 µmol/pH·mL media.

* * * * *